United States Patent [19]

Oswald et al.

[11] 4,067,972

[45] Jan. 10, 1978

[54] O-(METHYL OR ETHYL)-S-(PROPYL OR BUTYL)-O-ALKYL-(THIO/SULFINYL/SULFONYL)-METHYLPHENYL-THIOPHOSPHATES

[75] Inventors: Alexis A. Oswald, Mountainside; Paul L. Valint, Woodbridge, both of N.J.

[73] Assignee: Ciba-Geigy Corporation, Ardsley, N.Y.

[21] Appl. No.: 610,208

[22] Filed: Sept. 4, 1975

Related U.S. Application Data

[60] Division of Ser. No. 489,281, July 17, 1974, abandoned, which is a continuation of Ser. No. 326,731, Jan. 26, 1973, abandoned.

[30] Foreign Application Priority Data

Jan. 26, 1972   Switzerland ............... 1226/72
Oct. 5, 1972    Switzerland ............... 14600/72
Dec. 20, 1972   Switzerland ............... 18528/72

[51] Int. Cl.² ............... A01N 9/36; C07F 9/165
[52] U.S. Cl. ............... 424/216; 260/940; 260/948; 260/949; 260/955; 260/965; 424/210; 424/224
[58] Field of Search ............... 260/948; 424/216

[56] References Cited

U.S. PATENT DOCUMENTS

| | | | |
|---|---|---|---|
| 3,337,653 | 8/1967 | Szabo et al. ............... | 260/948 |
| 3,660,543 | 5/1972 | Mueller et al. ............... | 260/948 |
| 3,663,665 | 5/1972 | Kume et al. ............... | 260/978 |
| 3,725,546 | 4/1973 | Tsuchiya et al. ............ | 260/954 UX |
| 3,927,148 | 12/1975 | Oswald et al. ............... | 260/948 |

FOREIGN PATENT DOCUMENTS 631,472   11/1961   Canada ............... 260/948

Primary Examiner—Anton H. Sutto
Attorney, Agent, or Firm—Frederick H. Rabin

[57] ABSTRACT

Thiophosphoric acid phenyl esters of the formula

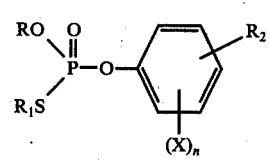

wherein R represents alkyl with 1 to 2 carbon atoms, $R_1$ represents alkyl with 3 to 4 carbon atoms, $R_2$ represents alkylthio with 1 to 4 carbon atoms, alkylthiomethyl with 1 to 4 carbon atoms, alkylsulfinyl with 1 to 4 carbon atoms, alkylsulfinylmethyl with 1 to 4 carbon atoms, alkylsulfonyl with 1 to 4 carbon atoms, alkylsulfonylmethyl with 1 to 4 carbon atoms, $-S(CH_2)_mCN$, $-S(CH_2)_mCl$, $SCF_3$

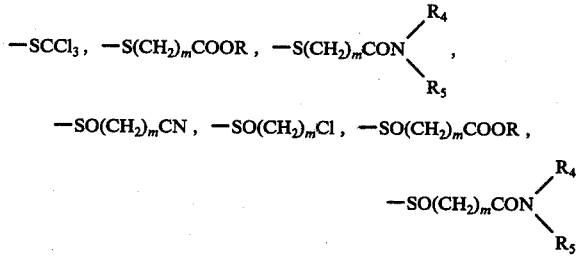

$R_3$ represents $C_1$ to $C_4$ alkyl, $R_4$ and $R_5$ each represents hydrogen or $C_1$ to $C_4$ alkyl, m is 1 or 2, n is 0, 1 or 2, and X represents alkyl with 1 to 4 carbon atoms or halogen, a process for their manufacture and their use in pest control.

10 Claims, No Drawings

O-(METHYL OR ETHYL)-S-(PROPYL OR BUTYL)-O-ALKYL-(THIO/SULFINYL/SULFONYL)-METHYLPHENYL-THIOPHOSPHATES

This is a division of application Ser. No. 489,281 filed on July 17, 1974, which is a continuation of application Ser. No., 326,731 filed in Jan. 26, 1973, both now abandoned.

The present invention relates to thiophosphoric acid phenyl esters, a process for their manufacture and their use in pest control. The compounds have the formula

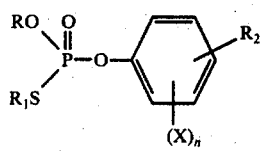

wherein R represents alkyl with 1 to 2 carbon atoms, $R_1$ represents alkyl with 3 to 4 carbon atoms, $R_2$ is a $C_1$ to $C_8$ saturated substituted or nonsubstituted aliphatic radical containing sulfur in the form of a sulfide, sulfoxide or sulfone group. The sulfur is preferably inserted between the phenyl and the alkyl group as a phenylthioether, phenylsulfoxide or phenylsulfone or is present as a benzylic thioether.

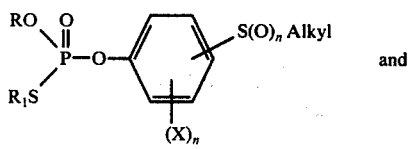

and

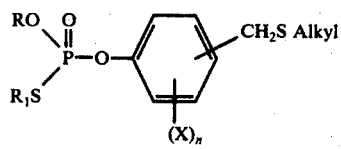

The substituted aliphatic radical includes halogenated, cyano, carboxylic acid ester, carboxylic acid amide derivatives. More preferably $R_2$ represents alkylthio with 1 to 4 carbon atoms, alkylthiomethyl with 1 to 4 carbon atoms, alkylsulfinyl with 1 to 4 carbon atoms, alkylsulfinylmethyl with 1 to 4 carbon atoms, alkylsulfonyl with 1 to 4 carbon atoms, alkylsulfonylmethyl with 1 to 4 carbon atoms, $-S(CH_2)_mCN$, $-S(CH_2)_mCl$, $-SCF_3$,

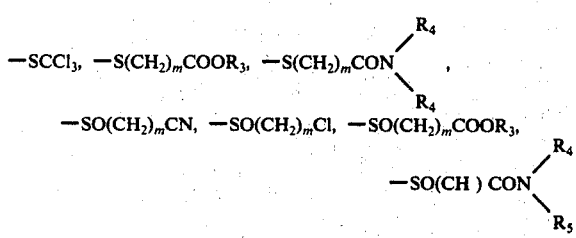

$R_3$ represents $C_1$ to $C_4$ alkyl, $R_4$ to $R_5$ each represents hydrogen or $C_1$ to $C_4$ alkyl, $m$ is 1 or 2, $n$ is 0, 1 or 2, and X represents alkyl with 1 to 4 carbon atoms or halogen. By halogen is meant fluorine, chlorine, bromine or iodine, but in particular chlorine and bromine.

Thionophosphate esters related to the thiolphosphate esters of the present application such as

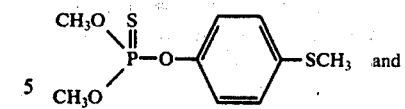

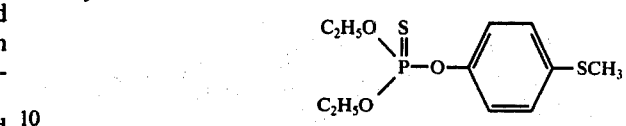

are well known insecticides with high mammalian toxicity as described in the monograph entitled "Chemie der Bflanzenschutz-und Schadlings-Bekampfungsmittel", Vol. 1, edited by R. Wegler and published by Springer Verlag, New York in 1970, pages 312 to 316. The surprising property of the present, novel thiolphosphate compounds such as

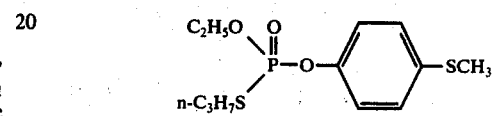

is the reduced toxicity towards warmblooded animals accompanied by the broadening of the spectrum of pesticidal effectiveness. The unexpected desirable properties of the present compound largely depend on the thiono-Po to thiolphosphate isomerization. However, as an added surprise they also depend on the selection of the R and $R_1$ groups. The R group should be methyl or ethyl, preferably ethyl. The $R_1$ group should be propyl or butyl, preferably n-propyl or primary isobutyl.

The alkyl, alkenyl or alkinyl groups represented by R to $R_5$ may be straight-chain or branched, in which case the alkyl groups $R_3$ to $R_5$ contain preferably 1 to 5 carbon atoms in the chain Examples of such groups include: methyl, ethyl, propyl, isopropyl, n-, i-, sec. and tert. butyl, n-pentyl and its isomers, allyl, methallyl, propargyl, isobutinyl:

Compounds which on account of their activity are a focal point of interest are those of the formula I, wherein R represents methyl or ethyl, $R_1$ represents n-propyl, isopropyl or primary i-butyl and $R_2$ represents methylthio, methylsulphinyl, methylthiomethyl, methylsulphonyl, trichloromethylthio, trifluoromethylthio,

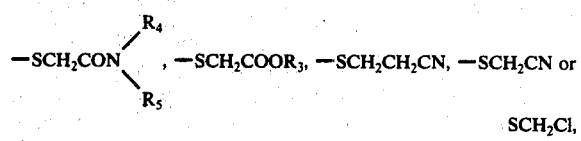

X represents methyl or chlorine, $R_3$ represents methyl or ethyl, $R_4$ and $R_5$ each represents hydrogen or methyl, and $n$ is 0 to 2.

Particularly preferred compounds, however, are those of the formula I wherein R represents ethyl, $R_1$ represents propyl, primary isobutyl, isopropyl, and $R_2$ represents methylthio, methylsulphinyl, methylthiomethyl, methylsulphonyl, trichloromethylthio, trifluoromethylthio;

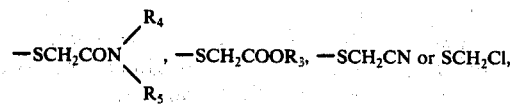

X represents methyl or chlorine, $R_3$ represents methyl or ethyl, $R_4$ and $R_5$ each represents hydrogen or methyl and $n$ is 0 to 2. The compounds of the formula I can be manufactured by the following methods:

1a)
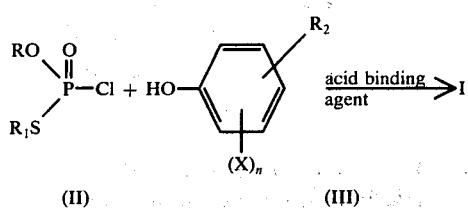

1b)
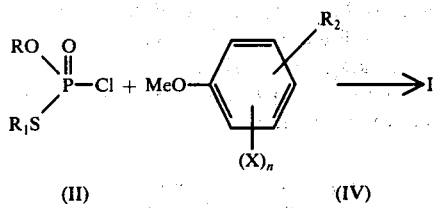

2)
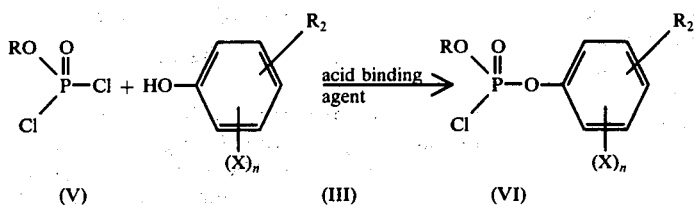

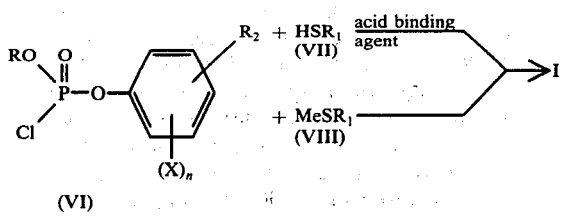

3)
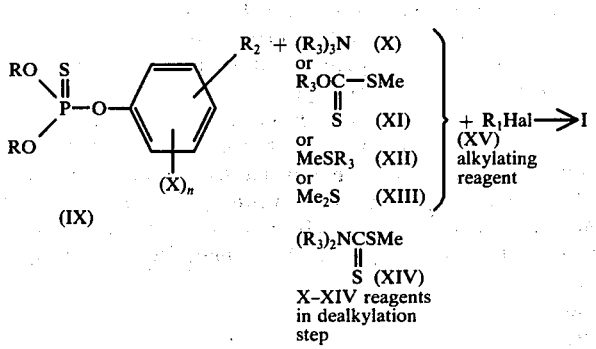

In the formulae II to XV, R, $R_1$, $R_2$, X and $n$ have the meanings given for the formula I, Me represents an alkali metal, in particular sodium or potassium or ammonium or alkyl-ammonium, $R_3$ represents hydrogen or alkyl with 1 to 4 carbon atoms and Hal represents a halogen atom, such as chlorine, bromine or iodine on a primary or secondary alkyl group.

Suitable acid binding agents are: tertiary amines, e.g. trialkylamines, pyridine, dialkylanilines; inorganic bases, such as hydrides, hydroxides; carbonates and bicarbonates of alkali and alkaline earth metals. During the reactions it is sometimes necessary to use a catalyst, for example copper or copper chloride. Processes 1, 2, and 3 can be carried out at normal pressure and in solvents or diluents.

Examples of suitable solvents or diluents are: ether and ethereal compounds, such as diethyl ether, dipropyl ether, dioxan, tetrahydrofuran; amides, such as N,N-dialkylated carboxylic acid amides; aliphatic, aromatic and halogenated hydrocarbons, in particular benzene, toluene, xylenes, chloroform, chlorobenzene; nitriles, such as acetonitrile; dimethyl sulphoxide; alcohols, such as ethanol and ketones, such as acetone, ethyl methyl ketone, water.

Some of the starting materials of the formulae, II, III, IV, V and IX are known or it is possible to manufacture them in analogous manner to known methods, e.g. those described in German Auslegeschriften Nos. 1051863, 1063177, 1088980 or 1298990.

The active substances of the formula I are suitable for combating animal and plant pests of the diverse kinds. They can be used, for example, as funistatic or bacteriostatic agents. But surprisingly they have a markedly better action against all development stages, e.g. eggs, larvae, pupae, nymphs and adults, of insects and representatives of the order Acarina, such as mites and ticks then e.g. analogous compounds of German Pat. No. 1138041. Thus the compounds of the formula I can be used against insects of the families:

| | |
|---|---|
| Tettigonidae | Tenebrionidae |
| Gryllidae | Chrysomelidae |
| Gryllotalpidae | Bruchidae |
| Blattidae | Tineidae |
| Reduviidae | Noctuidae |
| Phyrrhocoriae | Lymatriidae |
| Cimicidae | Pyraiidae |
| Delphacidae | Culicidae |
| Aphididae | Tipulidae |
| Diaspididae | Stomoxydae |
| Pseudococcidae | Trypetidae |
| Scarabaeidae | Muscidae |
| Dermestidae | Calliphoridae and |
| Coccinellidae | Pulicidae |
| Acarida of the families: | |
| Ixodidae | Argasidae |
| Tetranychidae and | Dermanyssidae. |

Similarly the compounds of the present invention show superior activity against insects of the order of Lepidoptera.

The insecticidal and/or acaricidal action can be substantially broadened and adapted to suit the particular circumstances by the addition of other insecticides and/or acaricides.

Suitable additives include, for example, the following active substances:

ORGANIC PHOSPHORUS COMPOUNDS

Bis-O,O-diethylphosphoric acid anhydride (TEPP)
Dimethyl-(2,2,2-trichloro-1-hydroxyethyl)-phosphonate (TRICHLORFON)
1,2-dibromo-2,2-dichloroethyldimethylphosphate (NALED)
2,2-dichlorovinyldimethylphosphate (DICHLORVOS)
2-methoxycarbamyl-1-methylvinyldimethylphosphate (MEVINPHOS)
Dimethyl-1-methyl-2-(methylcarbamoyl)-vinylphosphate cis (MONOCROTOPHOS)
3-(dimethoxyphosphinyloxy)-N,N-dimethyl-cis-crotonamide (DICROTOPHOS)
2-chloro-2-diethylcarbamoyl-1-methylvinyldimethylphosphate (PHOSPHAMIDON)
O,O-diethyl-O(or S)-2-(ethylthio)-ethylthiophosphate (DEMETON)
S-ethylthiocethyl-O,O-dimethyl-dithiophosphate (THIOMETON)
O,O-diethyl-S-ethylmercaptomethyldithiophosphate (PHORATE)
O.O-diethyl-S-2-(ethylthio)ethyldithiophosphate (DISULFOTON)
O,O-dimethyl-S-2-(ethylsulphinyl)ethylthiophosphate (OXYDEMETON METHYL)
O,O-dimethyl-S-(1,2-dicarbethoxyethyldithiophosphate (MALATHION)
O,O,O,O-tetraethyl-S,S'-methylene-bis-dithiophosphate (ETHION)
O-ethyl-S,S-dipropyldithiophosphate
O,O-dimethyl-S-(N-methyl-N-formylcarbamoylmethyl)-dithiophosphate (FORMOTHION)
O,O-dimethyl-S-(N-methylcarbamoylmethyl)dithiophosphate (DIMETHOATE)
O,O-dimethyl-O-p-nitrophenylthiophosphate (PARATHION-METHYL)
O,O-diethyl-O-p-nitrophenylthiophosphate (PARATHION)
O-ethyl-O-p-nitrophenylphenylthiophosphate (EPN)
O,O-dimethyl-O-(4-nitro-m-tolyl)thiophosphate (FENITROTHION)
O,O-dimethyl-O-2,4,5-trichlorophenylthiophosphate (RONNEL)
O-ethyl-0,2,4,5-trichlorophenylethylthiophosphate (TRICHLORONATE)
O,O-dimethyl-O-2,5-dichloro-4-bromophenylthiophosphate (BROMOPHOS)
O,O-dimethyl-O-(2,5-dichloro-4-iodophenyl)-thiophosphate (JODOFENPHOS)
4-tert.butyl-2-chlorophenyl-N-mthyl-O-methylamidophosphate (CRUFOMATE)
O,O-dimethyl-O-(3-methyl-4-methylmercaptophenyl)thiophosphate (FENTHION)
Isopropylamino-O-ethyl-O-(4-methylmercapto-3-methylphenly)-phosphate
O,O-diethyl-O-p-(methylsulphinyl)phenyl-thiophosphate (FENSULFOTHION)
O-p-(dimethylsulphamido)phenyl-O,O-dimethylthiophosphate (FAMPHUR)
O,O,O',O'-tetramethyl-O,O'-thiodi-p-phenylenethiophosphate
O-ethyl-S-phenyl-ethyldithiophosphate
O,O-dimethyl-O-(α-methylbenzyl-3-hydroxycrotonyl) phosphate
2-chloro-1-(2,4-dichlorophenyl)vinyl-diethylphosphate (CHLORFENVINPHOS)
1-chloro-1-(2,4,5-trichlorophenyl)vinyl-dimethylphosphate
O-[2-chloro-1-(2,5-dichlorophenyl]vinyl-O,O-diethylthiophosphate
Phenylglyoxylonitriloxime-O,O-diethylthiophosphate (PHOXIM) O,O-diethyl-O-(3-chloro-4-methyl-2-oxo-2-H-1-benzopyran-7-yl)-thiophosphate (COUMAPHOS)
2,3-p-dioxanedithiol-S,S-bis(O,O-diethyldithiophosphate) (DIOXATHION)
5-[(6-chloro-2-oxo-3-benzoxazolinyl) methyl]O,O-diethyldithiophosphate (PHOSALONE)
2-(diethoxyphosphinylimino)-1,3-dithiolane
O,O-dimethyl-S-[2-methoxy-1,3,4-thiadiazol-5-(4H)-onyl-(4)-methyl]dithiophosphate
O,O-dimethyl-S-phthalimidomethyl-dithiophosphate (IMIDAN) O,O-diethyl-O-(3,5,6-trichloro-2-pyridyl)-thiophosphate
O,O-diethyl-O-2-pyrazinylthiophosphate (THIONAZIN) O,O-diethyl-O-(2-isopropyl-4-methyl-6-pyrimidyl)thiophosphate (DIAZINON)
O,O-diethyl-O-(2-quinoxalyl)thiophosphate
O,O-dimethyl-S-(4-oxo-1,2,3-benzotriazin-3(4H)-ylmethyl)dithiophosphate (AZINPHOSMETHYL)
O,O-diethyl-S-(4-oxo-1,2,3-benzotriazin-3(4H)-ylmethyl)dithiophosphate (AZINPHOSETHYL)
S-[(4,6-diamino-s-triazin-2-yl)methyl]-O,O-dimethyldithiophosphate (MENAZON)
O,O-dimethyl-O-(3-chloro-4-nitrophenyl)thiophosphate (CHLORTHION)
O,O-dimethyl-O(or S)-2-(ethylthicethyl)thiophosphate (DEMETON-S-METHYL)
2-(O,O-dimethyl-phosphoryl-thiomethyl)-5-methoxy-pyrone-4-3,4-dichloroenzyl-triphenylphosphoniumchloride
O,O-diethyl-S-(2,5-dichlorophenylthiomethyl)dithiophosphate (PHENKAPTON)
O,O-diethyl-O-(4-methyl-cumarinyl-7-)-thiophosphate (POTASAN) 5-amino-bis(dimethylamido)phosphinyl-3-phenyl-1,2,4-triazole (TRIAMIPHOS)
N-methyl-5-(O,O-dimethylthiolphosphoryl)-3-thiavaleramide (VAMIDOTHION)

O,O-diethyl-O-[2-dimethylamino-4-methylpyrimidyl-(6)]-thiophosphate (DIOCTHYL)

O,O-dimethyl-S-(methylcarbamoylmethyl)-thiophosphate (OMETHOATE) O-ethyl-O-(8-quinolinyl)-phenylthiophosphonate (OXINOTHIOPHOS) O-methyl-S-methyl-amidothiophosphate (MONITOR) O-methyl-O-(2,5-dichloro-4-bromophenyl)-benzothiophosphate (PHOSVEL)

O,O,O,O- tetrapropyldithiophosphate 3-(dimethoxyphosphinyloxy)-N-methyl-N-methoxy-cis-crotonamide O,O-dimethyl-S-(N-ethylcarbamoylmethyl)dithiophosphate (ETHOATE-METHYL)

O,O-diethyl-S-(N-isopropylcarbamoylmethyl)-dithiophosphate (PROTHOATE)

S-N-(1-cyano-1-methylethyl)carbamoylmethyldiethylthiolphosphate (CYANTHOATE)

S-(2-acetamidoethyl)-O,O-dimethyldithiophosphate Hexamethylphosphoric acid triamide (MEMPA) O,O-dimethyl-O-(2-chloro-4-nitrophenyl)thiophosphate (DICAPTHON) O,O-dimethyl-O-p-cyanophenyl thiophosphate (CYANOX)

O-ethyl-O-p-cyanophenylthiophosphonate O,O-diethyl-O-2,4-dichlorophenylthiophosphate (DICHLORFENTHION) 0,2,4-dichlorophenyl-O-methylisopropylamidothiophosphate O,O-diethyl-O-2,5-dichloro-4-bromophenylthiophosphate (BROMOPHOS-ETHYL)

dimethyl-p-(methylthio)phenylphosphate O,O-dimethyl-O-p-sulphamidophenylthiophosphate O-[p-(p-chlorophenyl)azophenyl]O,O-dimethylthiophosphate (AZOTHOATE)

O-ethyl-S-4-chlorophenyl-ethyldithiophosphate O-isobutyl-S-p-chlorophenyl-ethyldithiophosphate O,O-dimethyl-S-p-chlorophenylthiophosphate O,O-dimethyl-S-(p-chlorophenylthiomethyl)dithiophosphate O,O-diethyl-p-chlorophenylmercaptomethyl-dithiophosphate (CARBOPHENOTHION)

O,O-diethyl-S-p-chlorophenylthiomethyl-thiophosphate O,O-dimethyl-S-(carbethoxy-phenylmethyl)dithiophosphate (PHENTHOATE)

O,O-diethyl-S-(carbofluorethoxy-phenylmethyl)-dithiophosphate O,O-dimethyl-S-carboisopropoxyphenylmethyl)-dithiophosphate O,O-diethyl-7-hydroxy-3,4-tetramethylene-coumarinyl-thiophosphate (COUMITHOATE)

2-methoxy-4-H-1,3,2-benzodioxaphosphorin-2-sulphide

O,O-diethyl-O-(5-phenyl-3-isooxazolyl)thiophosphate 2-(diethoxyphosphinylimino)-4-methyl-1,3-dithiolane tris-(2-methyl-1-aziridinyl)-phosphine oxide (ME-TEPA) S-(2-chloro-1-phthalimidoethyl)-O,O-diethyldithiophosphate N-hydroxynaphthalimide-diethylphosphate dimethyl-3,5,6-trichloro-2-pyridylphosphate O,O-dimethyl-O-(3,5,6-trichloro-2-pyridyl)thiophosphate S-2-(ethylsulphonyl)ethyl dimethylthiolphosphate (DIOXYDEMETON-S-METHYL)

diethyl-S-2-(ethylsulphinyl)ethyl dithiophosphate (OXIDISULFOTON) bis-O,O-diethylthiophosphoric acid anhydride (SULFOTEP) dimethyl-1,3-di(carbomethoxy)-1-propen-2-yl-phosphate dimethyl-(2,2,2-trichloro-1-butyroyloxyethyl)phosphate (BUTONATE)

O,O-dimethyl-O-(2,2-dichloro-1-methoxy-vinyl)-phosphate bis-(dimethylamido)fluorphosphate (DIMEFOX) 3,4-dichlorobenzyl-triphenylphosphoniumchloride dimethyl-N-methoxymethylcarbamoylmethyldithiophosphate (FORMOCARBAM)

O,O-diethyl-O-(2,2-dichloro-1-chloroethoxyvinyl)-phosphate O,O-dimethyl-O-(2,2-dichloro-1-chloroethoxyvinyl)phosphate O-ethyl-S,S-diphenyldithiolphosphate O-ethyl-S-benzyl-phenyldithiophosphonate O,O-diethyl-S-benzyl-thiolphosphate O,O-dimethyl-S-(4-chlorophenylthiomethyl)dithiophosphate (METHYLCARBOPHENOTHION)

O,O-dimethyl-S-(ethylthiomethyl)dithiophosphate diisopropylaminofluorophosphate (MIPAFOX) O,O-dimethyl-S-(morpholinylcarbamoylmethyl)dithiophosphate (MORPHOTHION)

bismethylamido-phenylphosphate O,O-dimethyl-S-(benzene sulphonyl)dithiophosphate O,O-dimethyl-(S and O)-ethylsulphinylethylthiophosphate O,O-diethyl-O-4-nitrophenylphosphate triethoxy-isopropoxy-bis(thiophosphinyl)disulphide
2-methoxy-4H-1,3,2-benzodioxaphosphorin--2-oxide octamethylpyrophosphoramide (SCHRADAN) bis-(dimethoxythiophosphinylsulphido)-phenylmethane N,N,N',N'-tetramethyldiamidofluorophosphate (DIMEFOX) O-phenyl-O-p-nitrophenyl-methanethiophosphonate (COLEP) O-methyl-O-(2-chloro-4-tert-butyl-phenyl)-N-methylamidothiophosphate (NARLENE)

O-ethyl-O-(2,4-dichlorophenyl)-phenylthiophosphonate O,O-diethyl-O-(4-methylmercapto-3,5-dimethylphenyl)-thiophosphate 4,4'-bis-(O,O-dimethylthiophosphoryloxy)-diphenyl disulphide O,O-di-($\beta$-chloroethyl)-O-(3-chloro-4-methyl-coumarinyl-7)-phosphate S-(1-phthalimidoethyl)-O,O-diethyldithiophosphate O,O-dimethyl-O-(3-chloro-4-diethylsulphamylphenyl)-thiophosphate O-methyl-O-(2-carbisopropoxyphenyl)-amidothiophosphate 5-(O,O-dimethylphosphoryl)-6-chloro-bicyclo(3.2.0)-heptadiene(1,5) O-methyl-O-(2-i-propoxycarbonyl-1-methylvinyl)-ethylamidothiophosphate.

Nitrophenols and derivatives 4,6-dinitro-6-methylphenol, sodium salt [Dinitrocresol] dinitrobutylphenol-(2,2',2")-triethanolamine salt 2-cyclohexyl-4,6-dinitrophenyl [Dinex] 2-(1-methylheptyl)-4,6-dinitrophenyl-crotonate [Dinocap] 2-sec.-butyl-4,6-dinitrophenyl-3-methyl-butenoate [Binapacryl] 2-sec.-butyl-4,6-dinitrophenyl-cyclopropionate 2-sec.-butyl-4,6-dinitrophenylisopropylcarbonate [Dinobuton]

Miscellaneous pyrethin I
pyrethin II
3-allyl-2-methyl-4-oxo-2-cyclopentan-1-yl-chrysanthemumate (Allethrin)
6-chloropiperonyl-chrysanthemumate (Barthrin)
2,4-dimethylbenzyl-chrysanthemumate (Dimethrin)
2,3,4,5-tetrahydrophthalimidomethylchrysanthemumate
4-chlorobenzyl-4-chlorophenylsulphide [Chlorobensid]
6-methyl-2-oxo-1,3-dithiolo-[4,5-b]-quinoxaline (Quinomethionate)
(I)-3-(2-furfuryl)-2-methyl-2-methyl-4-oxocyclopent-2-enyl(I)-(cis+trans)-chrysanthemum-monocarboxylate [Furethrin]
2-pivaloyl-indane-1,3-dione [Pindon]
N'-(4-chloro-2-methylphenyl)-N,N-dimethylformamidine [Chlorophenamidin]
4-chlorobenzyl-4-fluorophenyl-sulphide [Fluorobenside]

5,6-dichloro-1-phenoxycarbamyl-2-trifluoromethyl-benzimidazole [Fenozaflor]
p-chlorophenyl-p-chlorobenzenesulphonate [Ovex]
p-chlorophenyl-benzenesulphonate [Fenson]
p-chlorophenyl-2,4,5-trichlorophenylsulphone [Tetradifon]
p-chlorophenyl-2,4,5-trichlorophenylsulphide [Tetrasul]
p-chlorobenzyl-p-chlorophenylsulphide [Chlorobenside]
2-thio-1,3-dithiolo-(5,6)-quinoxaline [Thiochinox]
prop-2-ynyl-(4-t-butylphenoxy)-cyclohexylsulphite [Propargil].

Formamidines 1-dimethyl-2-(2'-methyl-4'-chlorophenyl)-formamidine (CHLORPHENAMIDIN)
1-methyl-2-2,'-methyl-4'-chlorophenyl)-formamidine
1-methyl-2-(2'-methyl-4'-bromophenyl)-formamidine
1-methyl-2-(2',4'-dimethylphenyl)-formamidine
1-n-butyl-1-methyl-2-(2'-methyl-4'-chlorophenyl)-formamidine
1-methyl-1-(2'-chloroaniline-methylene)-formamidine
2-(2''-methyl-4''-chlorophenyl-formamidine
1-n-butyl-2-(2'-methyl-4'-chlorophenyl-imino)-pyrolidine.

Urea

N-2-methyl-4-chlorophenyl-N',N'-dimethyl-thiourea.

Carbamates 1-naphthyl-N-methylcarbamate (CARBARYL)
2-butinyl-4-chlorophenylcarbamate
4-dimethylamino-3,5-xylyl-N-methylcarbamate
4-dimethylamino-3-tolyl-N-methylcarbamate (AMINOCARB)
4-methylthio-3,5-xylyl-N-methylcarbamate (METHIOCARB)
3,4,5-trimethylphenyl-N-methylcarbamate
2-chlorophenyl-N-methylcarbamate (CPMC)
5-chloro-6-oxo-2-norborane-carbonitrile-O-(methylcarbamoyl)-oxime
1-(dimethylcarbamoyl)-5-methyl-3-pyrazolyl-N,N-dimethylcarbamate (DIMETILAN)
2,3-dihydro-2,2-dimethyl-7-benzofuranyl-N-methylcarbamate (CARBOFURAN)
2-methyl-2-methylthio-propionaldehyde-O-(methylcarbamoyl)-oxime (ALDICARB)
8-quinaldyl-N-methylcarbamate and its salts
methyl-2-isopropyl-4-(methylcarbamoyloxy)carbanilate
m-(1-ethylpropyl)phenyl-N-methylcarbamate
3,5-di-tert.butyl-N-methylcarbamate
m-(1-methylbutyl)phenyl-N-methylcarbamate
2-isopropylphenyl-N-methylcarbamate
2-sec.butylphenyl-N-methylcarbamate
m-tolyl-N-methylcarbamate
2,3-xylyl-N-methylcarbamate
3-isopropylphenyl-N-methylcarbamate
3-tert.butylphenyl-N-methylcarbamate
3-sec.butylphenyl-N-methylcarbamate
3-isopropyl-5-methylphenyl-N-methylcarbamate (PROMECARB)
3,5-diisopropylphenyl-N-methylcarbamate
2-chloro-5-isopropylphenyl-N-methylcarbamate
2-chloro-4,5-dimethylphenyl-N-methylcarbamate
2-(1,3-dioxolan-2-yl)phenyl-N-methylcarbamate (DIOXACARB)
2-(4,5-dimethyl-1,3-dioxolan-2-yl)phenyl-N-methylcarbamate
2-(1,3-dioxolan-2-yl)phenyl-N,N-dimethylcarbamate
2-(1,3-dithiolan-2-yl)-N,N-dimethylcarbamate
2-(1,3-dithiolan-2-yl)phenyl-N,N-dimethylcarbamate
2-isopropoxyphenyl-N-methylcarbamate (APROCARB)
2-(2-propinyloxy)phenyl-N-methylcarbamate
3-(2-propinyloxy)phenyl-N-methylcarbamate
2-dimethylaminophenyl-N-methylcarbamate
2-diallylaminophenyl-N-methylcarbamate
4-diallylamino-3,5-xylyl-N-methylcarbamate (ALYXICARB)
4-benzothienyl-N-methylcarbamate
2,3-dihydro-2-methyl-7-benzofuranyl-N-methylcarbamate
3-methyl-1-phenylpyrazol-5-yl-N,N-dimethylcarbamate
1-isopropyl-3-methylpyrazol-5-yl-N,N-dimethylcarbamate (ISOLAN)
2-dimethylamino-5,6-dimethylpyrimidin-4-yl-M,N-dimethyl-carbamate
3-methyl-4-dimethylaminomethyleneiminophenyl-N-methylcarbamate
3,4-dimethylphenyl-N-methylcarbamate
2-cyclopentylphenyl-N-methylcarbamate
3-dimethylamino-methyleneiminophenyl-N-methylcarbamate (FORMETANATE) and its salts
1-methylthio-ethylimino-N-methylcarbamate (METHOMYL)
2-methylcarbamoyloximino-1,3-dithiolane
5-methyl-2-methylcarbamoyloximino-1,3-oxythiolane
2-(1-methoxy-2-propoxy)phenyl-N-methylcarbamate
2-(1-butin-3-yl-oxy)phenyl-N-methylcarbamate
1-dimethylcarbamyl-1-methylthio-O-methylcarbamyl-formoxime
1-(2'-cyanoethylthio)-O-methylcarbamyl-acetaldoxime
1-methylthio-O-carbamyl-acetaldoxime
O-(3-sec.butylphenyl)-N-phenylthio-N-methylcarbamate
2,5-dimethyl-1,3-dithiolane-2-(O-methylcarbamyl)-aldoxime)
O-2-diphenyl-N-methylcarbamate
2-(N-methylcarbamyl-oximino)-3-chloro-bicyclo[2.2.1]heptane
2-(N-methylcarbamyl-oximino)-bicyclo[2.2.1]heptane
3-isopropylphenyl-N-methyl-N-chloroacetal-carbamate
3-isopropylphenyl-N-methyl-N-methylthiomethyl-carbamate O-(2,2-dimethyl-4-chloro-2,3-dihydro-7-benzofuranyl)-N-methylcarbamate
O-(2,2,4-trimethyl-2,3-dihydro-7-benzofuranyl)-N-methylcarbamate
O-naphthyl-N-methyl-N-acetal-carbamate
O-5,6,7,8-tetrahydronaphthyl-N-methyl-carbamate
3-isopropyl-4-methylthio-phenyl-N-methylcarbamate
3,5-dimethyl-4-methoxy-phenyl-N-methylcarbamate
3-methoxymethoxy-phenyl-N-methylcarbamate
3-allyloxyphenyl-N-methylcarbamate
2-propargyloxymethoxy-phenyl-N-methyl-carbamate 2-allyloxyphenyl-N-methyl-carbamate
4-methoxycarbonylamino-3-isopropylphenyl-N-methyl-carbamate
3,5-dimethyl-4-methoxycarbonylamino-phenyl-N-methyl-carbamate
2-γ-methylthiopropylphenyl-N-methyl-carbamate
3-α-methoxymethyl-2-propenyl)-phenyl-N-methyl-carbamate 2-chloro-5-tert.-butyl-phenyl-N-methyl-carbamate
4-(methyl-propargylamino-3,5-xylyl-N-methyl-carbamate
4-(methyl-γ-chloroallylamino)-3,5-xylyl-N-methyl-carbamate
4-(methyl-β-chloroallylamino)-3,5-xylyl-N-methyl-carbamate
1-(β-ethoxycarbonylethyl)-3-methyl-5-pyrazolyl-N,N-dimethylcarbamate
3-methyl-4-(dimethylamino-methylmercapto-methyleneimino)phenyl-N-methylcarbamate
1,3-bis(carbamoylthio)-2-(N,N-dimethylamino)-propanehydrochloride
5,5-dimethylhydroresorcinoldimethylcarbamate
2-[ethyl-propargylamino]-phenyl-N-methylcarbamate
2-[methyl-propargylamino]-phenyl-N-methylcarbamate
4-[dipropargylamino]-3-tolyl-N-methylcarbamate
4-[dipropargylamino]-3,5-xylyl-N-methylcarbamate
2-[allyl-isopropylamino]-phenyl-N-methylcarbamate
3-[allyl-isopropylamino]-phenyl-N-methylcarbamate Chlorinated Hydrocarbons γ-hexachlorocyclohexane [GAMMEXANE; LINDAN; γ HCH]
1,2,4,5,6,7,8,8-octachloro-3α,4,7,7α'-tetrahydro-4,7-methylene indane [CHLORDAN]
1,4,5,6,7,8,8-heptachloro,3α,4,7,7α-tetrahydro-4,7-methylene indane [HEPTACHLOR]
1,2,3,4,10,10-hexachloro-1,4,4α,5,8,8α-hexahydro-endo-1,4-exo-5,8-dimethanonaphthalene [ALDRIN]
1,2,3,4,10,10-hexachloro-6,7-epoxy-1,4,4α,5,6,7,8,8α-octahydro-exo-1,4,endo-5,8-dimethanonaphthalene [DIFLORIN]
1,2,3,4,10,10-hexachloro-5,7-epoxy-1,4,4α5,6,7,8,8α-octyhydro-endo-5,8-dimethanonaphthalene [ENDRIN]

The active substances of the formula I are also suitable for combating representatives of the division Thallophyta, e.g. viruses, bacteria and fungi. They thus possess fungicidal properties against phytopathogenic fungi on various cultivated plants, such as cereals, maize, rice, vegetables, ornamental plants, fruit trees, vines, farm products, etc.

With the new active substances it is possible to control or destroy fungi occurring on fruit, blossom, leaves, stems, tubers and roots, and from which parts of plants which grow later then also remain free. The active substances of the formula I are active in particular against phytopathogenic fungi belonging to the following classes:

Oomycetes, Zygomycetes, Ascomycetes, Basidiomycetes, Denteromycetes.

In addition, the new active substances can also be used for treating seeds, fruits, tubers etc., and protecting them from fungus infections, for example from smut fungi of all kinds, such as Ustilaginales, e.g. Ustilago, Tilletia, Urocystis, Turbicinia and Phoma types.

In addition to the above cited acaricides and insecticides, it is also possible to admix the active substances of the formula I with, for example, bactericides, fungistatic agents, bacteriostatic agents, nematocides and/or e.g. the following fungicides, in order to broaden the activity spectrum:

dodecylguanidine acetate (DODINE)
pentachloronitrobenzene (QUINTOZENE)
pentachlorophenol (PCP)
2-(1-methyl-n-propyl)-4,6-dinitrophenyl-2-methylcrotonate (BINAPACRYL)
2-(1-methyl-n-heptyl)-4,6-dinitrophenylcrotonate (DINOCAP)
2,6-dichloro-4-nitroaniline (DICHLORAN)
2,3,5,6-tetrachloro-benzoquinone (1,4) (CHLORANIL)
2,3-dichloro-naphthoquinone (1,4) (DICHLONE)
N-(trichloromethylthio) phthalimide (FOLPAT) N-(trichloromethylthio) cyclohex-4-ene-1,2-dicarboximide (CAPTAN)
N-(1,1,2,2-tetrachloroethylthio)cyclohex-4-ene-1,2-dicarboximide (CAPTAFOL)
N-methansulfonal-N-trichloromethylthio-chloroaniline
N' -dichlorofluoromethylthio-N,N-dimethyl-N' -phenylsulphamide (DICHLOFLUANID)
O-ethyl-S-benzyl-phenyldithiophosphate
O,O-diethyl-S-benzyl-thiolphosphate
disodium-ethylene-1,2-bis-dithiocarbamate (NABAM)
zinc-ethylene-1,2-bis-dithiocarbamate (ZINEB)
manganese-ethylene-1,2-bis-dithiocarbamate (polymeric) (MANEB)
tetramethylithiuramdisulphide (THIRAM)
1-oxy-3-acetyl-6-methyl-cyclohexene-(5)dione-(2,4) (DEHYDRO-ACETIC ACID)
8-hydroxyquinoline (8-QUINOLIN0L)
2-dimethylamino-6-methyl-5-n-butyl-4-hydroxypyrimidine
methyl-N-benzimidazole-2-yl-N-(butylcarbamoyl)-carbamate (BENOMYL)
2-ethylamino-6-methyl-5n-butyl-4-hydroxypyrimidine
2,3-dicyano-1,4-dithia-anthraquinone (DITHIANON)
2-(4-thiazolyl)-benzimidazole
3,5-dimethyltetrahydro-1,3,5-thiadiazine-2-thione (DAZOMET)
2,3-dihydro-5-carboxanilido-6-methyl-1,4-oxathine pentachlorobenzyl alcohol.

Furthermore, the compounds of the formula I are suitable for combating plant pathogenic nematodes.

The compounds of the formula I may be used as pure active substance or together with suitable carriers and/or additives. Suitable carriers and additives can be solid or liquid and correspond to the substances conventionally used in formulation technique such, for example, as solvents, dispersants, wetting agents, adhesives, thickeners, binders and/or fertilisers.

For application, the compounds of the formula I may be processed to dusts, emulsion concentrates, granules, dispersions, sprays, to solutions, or suspensions, in the conventional formulation which is commonly employed in application technology. Mention may also be made of cattle dips and spray races, in which aqueous preparations are used.

The agents according to the invention are manufactured in known manner by intimately mixing and/or grinding active substances of the formula I with the suitable carriers, optionally with the addition of dispersants or solvents which are inert towards the active substances. The active substances may take, and be used in, the following forms, Solid forms:

Dusts, tracking agents, granules, coated granules, impregnated granules and homogeneous granules. Liquid forms:

a. active substances which are dispersible in water: wettable powders, pasts, emulsions, b. solutions.

To manufacture solid forms (dusts, tracking agents), the active substances are mixed with solid carriers. Suitable carriers are, for example: kaolin, talcum, bolus, loess, chalk, limestone, ground limestone, attaclay, dolomite, diatomaceous earth, precipitated silica, alkaline earth silicates, sodium and potassium aluminium silicates (feldspar and mica), calcium and magnesium sulphates, magnesium oxide, ground synthetic materials, fertilisers, for example ammonium sulphate, ammonium phosphate, ammonium nitrate, urea, ground vegetable products, such as corn meal, bark dust, sawdust, nutshell meal, cellulose powder, residues of plant extractions, activated charcoal etc. These substances can either be used singly or in admixture with one another.

Granules can be very easily manufactured by dissolving an active substance of the formula I in an organic solvent and applying the resulting solution to a granulated material, for example attapulgite, $SiO_2$, granicalcium, bentonite etc. and then evaporating the solvent.

Polymer granules can also be manufactured by mixing the active substances of the formula I with polymerisable compounds (urea/formaldehyde; dicyandiamide/formaldehyde; melamine/formaldehyde or others), whereupon a mild polymerisation is carried out that does not affect the active substances and in the process of which the granulation is carried out during the gel formation. It is more advantageous to impregnate finished, porous polymer granules (urea/formaldehyde, polyacrylonitrile, polyester or others) which have a specific surface area and a favourable predeterminable adsorption/desorption ratio, with the active substances, for example in the form of their solutions (in a low boiling solvent) and to remove the solvent. Polymer granules of this kind in the form of microgranules having a bulk density of 300 g/liter to 600 g/liter can also be manufactured with the aid of atomisers. The dusting can be carried out from aircraft over extensive areas of cultures of useful plants.

It is also possible to obtain granules by compacting the carrier with the active substance and carriers and subsequently comminuting the product.

To these mixtures can also be added additives which stabilise the active substance and/or non-ionic, anionic and cationic surface active substances, which, for example, improve the adhesion of the active ingredients on plants or parts of plants (adhesives and agglutinants) and/or ensure a bettter wettability (wetting agents) and dispersibility (dispersing agents). Examples of suitable adhesives are the following: olein/chalk mixture, cellulose derivatives (methyl cellulose, carboxymethyl cellulose), hydroxyethyl glycol ethers of monoalkyl and dialkyl phenols having 5 to 15 ethylene oxide radicals per molecule and 8 to 9 carbon atoms in the alkyl radical, lignin sulphonic acids, their alkali metal and alkaline earth metal salts, polyethylene glycol ethers (carbowaxes), fatty alcohol polyethylene glycol ethers having 5 to 20 ethylene oxide radicals per molecule and 8 to 18 carbon atoms in the fatty alcohol moiety, condensation products of ethylene oxide/propylene oxide, polyvinyl pyrrolidones, polyvinyl alcohols, condensation products of urea and formaldehyde, and also latex products.

The water-dispersible concentrates of the active substance, i.e. wettable powders, pastes and emulsifiable concentrates, are agents which can be diluted with water to any concentration desired. They consist of active substance, carrier, optionally additives which stabilise the active substance, surface-active substance and anti-foam agents and, optionally, solvents.

Wettable powders and pastes are obtained by mixing and grinding the active substances with dispersing agents and pulverulent carriers in suitable apparatus until homogeneity is attained. Suitable carriers are, for example, those mentioned for the solid forms of application. In some cases it is advantageous to use mixtures of different carriers. As dispersing agents there can be used, for example, condensation products of sulphonated naphthalene and sulphonated naphthalene derivatives with formaldehyde, condensation products of naphthalene or naphthalene sulphonic acids with phenol and formaldehyde, as well as alkali, ammonium and alkaline earth metal salts of lignin sulphonic acid, in addition, alkylaryl sulphonates, alkali and alkaline earth metal salts of dibutyl naphthalene sulphonic acid, fatty alcohol sulphates such as salts of sulphated hexadecanols, heptadecanols, octadecanols, and salts of sulphated fatty alcohol glycol ethers, the sodium salt of oleoyl ethionate, the sodium salts of oleoyl methyl tauride, ditertiary acetylene glycols, dialkyl dilauryl ammonium chloride and fatty acid alkali and alkaline earth metal salts.

Suitable anti-foam agents are silicones.

The active substances are mixed, ground, sieved and strained with the additives cited hereinabove in such a manner that, the size of the solid particles does not exceed 0.02 to 0.04 $\mu$ in wettable powders, and 0.03 $\mu$ in pastes. To produce emulsifiable concentrates and pastes, dispersing agents such as those cited above, organic solvents, and water are used. Examples of suitable solvents are: alcohols, benzene, xylene, toluene, dimethyl sulphoxide, and mineral oil fractions which boil between 120° and 350° C. The solvents must be practically odourless, not phytotoxic, and inert to the active substances.

Furthermore, the agents according to the invention can be applied in the form of solutions. For this purpose the active substances or several substances of the general formula I are dissolved in suitable organic solvents, mixtures of solvents or in water. Aliphatic and aromatic hydrocarbons, chlorinated derivatives thereof, alkyl naphthalenes, and mineral oils singly or in admixture with each other, can be used as organic solvents.

The content of active substances in the above described agents is between 0.1% to 95%, in which connection it should be mentioned that, in the case of application from aircraft or some other suitable means of application, it is possible to use concentrations of up to 99.5% or even pure active substance.

The active substances of the formula I can, for example, be formulated as follows:

Dusts

The following substances are used to manufacture a) a 5% and b) a 2% dust:

a.

5 parts of active substance
95 parts of talcum b.
- 2 parts of active substance
- 1 part of highly disperse silicic acid
- 97 parts of talcum.

The active substances are mixed with the carriers and ground.

Granules

The following substances are used to produce 5% granules:
- 5 parts of active substance,
- 0.25 parts of epichlorohydrin,
- 0.25 parts of cetyl polyglycol ether,
- 3.50 parts of polyethylene glycol,
- 91 parts of kaolin (particle size 0.3 - 0.8 mm).

The active substance is mixed with epichlorohydrin and dissolved with 6 parts of acetone; the polyethylene glycol and acetyl polyglycol ether are then added. The thus obtained solution is sprayed on kaolin, and the acetone subsequently evaporated in vacuo.

Wettable powder:

The following constituents are used for the preparation of a) a 40%, b) and c) a 25%, and d) a 10% wettable powder:

a.
- 40 parts of active substance,
- 5 parts of sodium lignin sulphonate,
- 1 part of sodium dibutyl-naphthalene sulphonate,
- 54 parts of silicic acid.

b.
- 25 parts of active substance,
- 4.5 parts of calcium lignin sulphonate,
- 1.9 parts of Champagne chalk/hydroxyethyl cellulose mixture (1:1)
- 1.5 parts of sodium dibutyl naphthalene sulphonate,
- 19.5 parts of silicic acid,
- 19.5 parts of Champagne chalk,
- 28.1 parts of kaolin.

c.
- 25 parts of active substance,
- 2.5 parts of isooctylphenoxy-polyoxyethylene-ethanol,
- 1.7 parts of Champagne chalk/hydroxyethyl cellulose mixture (1:1),
- 8.3 parts of sodium aluminium silicate,
- 16.5 parts of kieselguhr,
- 46 parts of kaolin.

d.
- 10 parts of active substance,
- 3 parts of a mixture of the sodium salts of saturated fatty alcohol sulphates,
- 5 parts of naphthalenesulphonic acid/formaldehyde condensate,
- 82 parts of kaolin.

The active substances are intimately mixed, in suitable mixers, with the additives, the mixture being then ground in the appropriate mills and rollers. Wettable powders are obtained which can be diluted with water to give suspensions of any desired concentration.

EMULSIFIABLE CONCENTRATES:

The following substances are used to produce a) a 10% and b) a 25% emulsifiable concentrate:

a.
- 10 parts of active substance,
- 3.4 parts of epoxidised vegetable oil,
- 13.4 parts of a combination emulsifier consisting of fatty alcohol polyglycol ether and alkylarylsulphonate calcium salt,
- 40 parts of dimethylformamide,
- 43.2 parts of xylene, b.
- 25 parts of active substance,
- 2.5 parts of epoxidised vegetable oil,
- 10 parts of an alkylarylsulphonate/fatty alcoholpolyglycol ether mixture
- 5 parts of dimethylformamide,
- 57.5 parts of xylene.

From these concentrates it is possible to produce, by dilution with water, emulsions of any desired concentration.

Spray

The following constituents are used to prepare a 5% spray:
- 5 parts of active substance,
- 1 part of epichlorohydrin,
- 94 parts of benzine (boiling limits 160° - 190° C).

EXAMPLE 1

O-ethyl-S-n-propyl-O-(4-methylmercapto-phenyl)-thiophosphate 12.2 g of triethylamine are added to a solution of 16.8 g of 4-methyl-mercapto-phenol in 150 ml of benzene. While stirring constantly, 24.4 g of thiophosphoric-O-ethyl-S-n-propyl-ester chloride are added dropwise at 10°-15° C. Stirring is then continued for 12 hours at room temperature. The mixture is washed with water, 3% sodium carbonate solution, and again with water, then dried over anhydrous sodium sulphate. The benzene is distilled off and the residue is purified by molecular distillation, to give 27 g of the compound of the formula

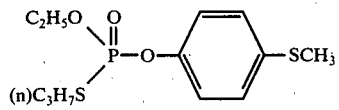

with a boiling point of 125° C/0.001 Torr; $n_D^{24} = 1.5501$
The following compounds are also manufactured in analogous manner:

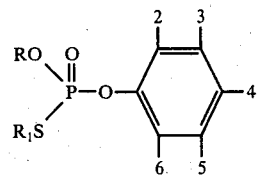

| R | $R_1$ | 2 | 3 | 4 | 5 | 6 | Data |
|---|---|---|---|---|---|---|---|
| —$C_2H_5$ | —$C_3H_7$(n) | H | —$CH_3$ | —$SCH_3$ | H | H | $n_D^{24} = 1,5509$ |
| —$C_2H_5$ | —$C_3H_7$(n) | H | —$CH_3$ | —$SCH_3$ | —$CH_3$ | H | |
| —$C_2H_5$ | —$C_3H_7$(n) | Cl | H | —$SCH_3$ | Cl | H | $n_D^{24} = 1,5737$ |

-continued

| R | R₁ | 2 | 3 | 4 | 5 | 6 | Data |
|---|---|---|---|---|---|---|---|
| —C₂H₅ | —C₃H₇(n) | H | —SCH₃ | H | H | H | |
| —C₂H₅ | —C₃H₇(n) | H | H | —SOCH₃ | H | H | $n_D^{24} = 1,5492$ |
| —C₂H₅ | —C₃H₇(n) | H | H | —SO₂CH₃ | H | H | $n_D^{24} = 1,5399$ |
| —C₂H₅ | —CH₂—CH=CH₂ | H | H | —SCH₃ | H | H | $n_D^{24} = 1,5558$ |
| —C₂H₅ | —C—C≡CH | H | H | —SCH₃ | H | H | $n_D^{24} = 1,5609$ |
| —C₂H₅ | —CH₂—⌬ | H | H | —SCH₃ | H | H | $n_D^{24} = 1,5748$ |
| —C₂H₅ | —C₃H₇(n) | —CH₂SCH₃ | H | H | H | H | $n_D^{24} = 1,5459$ |
| —C₂H₅ | —C₃H₇(n) | —CH₂SCH₃ | H | —CH₃ | H | H | |
| —C₂H₅ | —C₃H₇(n) | Br | H | —SCH₃ | H | H | $n_D^{24} = 1,5741$ |
| —C₂H₅ | —C₃H₇(n) | Br | H | —SCH₃ | H | Br | $n_D^{24} = 1,5998$ |
| —C₂H₅ | —C₃H₇(n) | H | —SCH₃ | Br | H | H | |
| —C₂H₅ | —C₃H₇(n) | Br | H | Br | —SCH₃ | H | |
| —C₂H₅ | —C₃H₇(n) | —SCH₃ | H | Br | H | H | |
| —C₂H₅ | —C₃H₇(n) | —SCH₃ | H | H | H | H | |
| —C₂H₅ | —C₃H₇(n) | —CH₂SCH₃ | H | H | H | H | |
| —C₂H₅ | —C₃H₇(n) | —CH₂SCH₃ | H | H | —CH₃ | H | |
| —C₂H₅ | —C₃H₇(n) | —CH₂CH₃ | H | —CH₃ | H | H | |
| —C₂H₅ | —C₃H₇(n) | H | H | —SCH₂Cl | H | H | $n_D^{24} = 1,5555$ |
| —C₂H₅ | —C₃H₇(n) | H | H | —SCH₂CN | H | H | $n_D^{24} = 1,5502$ |
| —C₂H₅ | —C₃H₇(n) | H | H | —SCH₂CH₂CN | H | H | |
| —C₂H₅ | —C₃H₇(n) | H | H | —SCH₂COOC₂H₅ | H | H | $n_D^{24} = 1,5354$ |
| —C₂H₅ | —C₃H₇(n) | H | H | —SCH₂CONH₂ | H | H | $n_D^{24} = 1,5601$ |
| —C₂H₅ | —C₃H₇(n) | H | H | —SCH₂CONHCH₃ | H | H | |
| —C₂H₅ | —C₃H₇(n) | H | H | —SCH₃ | H | H | |
| —C₂H₅ | —C₃H₇(n) | H | —CH₃ | —SCH₂Cl | H | H | $n_D^{24} = 1,5515$ |
| —C₂H₅ | —C₃H₇(n) | H | —CH₃ | —SCH₂CN | H | H | $n_D^{24} = 1,5507$ |
| —C₂H₅ | —C₃H₇(n) | H | —CH₃ | —SCH₂CH₂CN | H | H | |
| —C₂H₅ | —C₃H₇(n) | H | —CH₃ | —SCH₂COOC₂H₅ | H | H | $n_D^{24} = 1,5358$ |
| —C₂H₅ | —C₃H₇(n) | H | —CH₃ | —SCH₂CONH₂ | H | H | |
| —C₂H₅ | —C₃H₇(n) | H | —CH₃ | —SCH₂CONHCH₃ | H | H | |
| —C₂H₅ | —C₅H₁₁(n) | H | H | —SCH₃ | H | H | $n_D^{24} = 1,5395$ |
| —C₂H₅ | —C₅H₁₁(n) | H | —CH₃ | —SCH₃ | H | H | |
| —C₂H₅ | —CH₂—CH=CH₂ | H | —CH₃ | —SCH₃ | H | H | |
| —C₂H₅ | —CH₂—C≡CH | H | —CH₃ | —SCH₃ | H | H | |
| —C₂H₅ | —C₃H₇(n) | H | —CH₃ | —SCCl₃ | H | H | |
| —C₂H₅ | —C₃H₇(n) | Cl | H | —SCH₃ | H | H | |
| —C₂H₅ | —C₃H₇(n) | Cl | H | —SCH₃ | H | Cl | |
| —C₂H₅ | —C₃H₇(n) | H | —CH₃ | —SOCH₃ | H | H | |
| —C₂H₅ | —C₃H₇(n) | H | —CH₃ | —SO₂CH₃ | H | H | |
| —C₂H₅ | CH₃—CH—CH₂—CH₃ | H | H | —SCH₃ | H | H | $n_D^{24} = 1,5481$ |
| —C₂H₅ | —C₃H₇(n) | Cl | H | —SOCH₃ | Cl | H | |
| —C₂H₅ | —C₃H₇(n) | Cl | H | —SO₂CH₃ | Cl | H | |
| —C₂H₅ | —C₃H₇(n) | Br | H | —SOCH₃ | H | H | |
| —C₂H₅ | —C₃H₇(n) | Br | H | —SO₂CH₃ | H | H | |

| R | R₁ | 2 | 3 | 4 | 5 | 6 |
|---|---|---|---|---|---|---|
| —C₂H₅ | —C₃H₇(n) | Br | H | —SOCH₃ | H | Br |
| —C₂H₅ | —C₃H₇(n) | Br | H | —SO₂CH₃ | H | Br |
| —C₂H₅ | —C₃H₇(n) | H | —SOCH₃ | H | H | H |
| —C₂H₅ | —C₃H₇(n) | H | —SO₂CH₃ | H | H | H |
| —C₂H₅ | —C₃H₇(n) | H | —SOCH₃ | Br | H | H |
| —C₂H₅ | —C₃H₇(n) | H | —SO₂CH₃ | Br | H | H |
| —C₂H₅ | —C₃H₇(n) | Br | H | Br | —SOCH₃ | H |
| —C₂H₅ | —C₃H₇(n) | Br | H | Br | —SO₂CH₃ | H |
| —C₂H₅ | —C₃H₇(n) | —SOCH₃ | H | Br | H | H |
| —C₂H₅ | —C₃H₇(n) | —SO₂CH₃ | H | Br | H | H |
| —C₂H₅ | —C₃H₇(n) | —SOCH₃ | H | H | H | H |
| —C₂H₅ | —C₃H₇(n) | —SO₂CH₃ | H | H | H | H |
| —C₂H₅ | —C₃H₇(n) | —CH₂SOCH₃ | H | H | H | H |
| —C₂H₅ | —C₃H₇(n) | —CH₂SO₂CH₃ | H | H | H | H |
| —C₂H₅ | —C₃H₇(n) | —CH₂SOCH₃ | H | —CH₃ | H | H |
| —C₂H₅ | —C₃H₇(n) | —CH₂SO₂CH₃ | H | —CH₃ | H | H |
| —C₂H₅ | —C₃H₇(n) | —CH₂SOCH₃ | H | —CH₃ | H | H |
| —C₂H₅ | —C₃H₇(n) | H | H | —SOCH₂Cl | H | H |
| —C₂H₅ | —C₃H₇(n) | H | H | —SO₂CH₂Cl | H | H |
| —C₂H₅ | —C₃H₇(n) | H | H | —SOCH₂CN | H | H |
| —C₂H₅ | —C₃H₇(n) | H | H | —SO₂CH₂CN | H | H |
| —C₂H₅ | —C₃H₇(n) | H | H | —SOCH₂CH₂CN | H | H |
| —C₂H₅ | —C₃H₇(n) | H | H | —SO₂CH₂CH₂CN | H | H |
| —C₂H₅ | —C₃H₇(n) | H | H | —SOCCl₃ | H | H |
| —C₂H₅ | —C₃H₇(n) | H | H | —SO₂Cl₃ | H | H |
| —C₂H₅ | —C₃H₇(n) | H | —CH₃ | —SOCH₂Cl | H | H |
| —C₂H₅ | —C₃H₇(n) | H | —CH₃ | —SO₂CH₂Cl | H | H |
| —C₂H₅ | —C₃H₇(n) | H | —CH₃ | —SOCH₂CN | H | H |
| —C₂H₅ | —C₃H₇(n) | H | —CH₃ | —SO₂CH₂CN | H | H |
| —C₂H₅ | —C₃H₇(n) | H | —CH₃ | —SOCH₃CH₂CN | H | H |
| —C₂H₅ | —C₃H₇(n) | H | —CH₃ | —SOCH₂COOC₂H₅ | H | H |
| —C₂H₅ | —C₃H₇(n) | H | —CH₃ | —SO₂CH₂COOC₂H₅ | H | H |
| —C₂H₅ | —C₃H₇(n) | H | —CH₃ | —SOCH₂CONHCH₃ | H | H |
| —C₂H₅ | —C₃H₇(n) | H | —CH₃ | —SO₂CH₂CONHCH₃ | H | H |
| —C₂H₅ | —C₅H₁₁(n) | H | H | —SOCH₃ | H | H |
| —C₂H₅ | —C₅H₁₁(n) | H | H | —SO₂CH₃ | H | H |

-continued

| R | R₁ | 2 | 3 | 4 | 5 | 6 |
|---|---|---|---|---|---|---|
| $-C_2H_5$ | $-C_5H_{11}(n)$ | H | H | $-SOCH_3$ | H | H |
| $-C_2H_5$ | $-C_5H_{11}(n)$ | H | H | $-SO_2CH_3$ | H | H |
| $-C_2H_5$ | $-C_3H_7(n)$ | Cl | H | $-SOCH_3$ | H | H |
| $-C_2H_5$ | $-C_3H_7(n)$ | Cl | H | $-SO_2CH_3$ | H | H |
| $-C_2H_5$ | $-C_3H_7(n)$ | Cl | H | $-SOCH_3$ | H | Cl |
| $-C_2H_5$ | $-C_3H_7(n)$ | Cl | H | $-SO_2CH_3$ | H | Cl |
| $-C_2H_5$ | $-CH_2CH(CH_3)_2$ | H | H | $SCH_3$ | H | H |
| $C_2H_5$ | $-C_3H_7(n)$ | H | $CH_3$ | $SCH_3$ | $CH_3$ | H |
| $C_2H_5$ | $-C_3H_7(n)$ | H | H | $SCF_3$ | H | H |
| $C_2H_5$ | $-C_3H_7(n)$ | H | H | $SCF_3$ | $CH_3$ | H |

EXAMPLE 2

A. Insecticidal ingest poision action

Tobacco and potato plants were sprayed with a 0.05% aqueous emulsion (obtained from a 10% emulsifiable concentrate).

After the coating had dried, the tobacco plants were populated with Egyptian cotton leaf worms (Spodoptera literalis) and the potato plants with Colorado potato beetle larvae (Leptinotarsa decemlineata). The test was carried out at 24° C and 60% relative humidity. In the above test, the compounds according to Example I displayed ingest poison action against Spodoptera literalis and Leptinotarsa decemlineata.

B. Systemic insecticidal action

To determine the systemic action, rooted bean plants (Vicia fabae) were put into a 0.01% aqueous active substance solution (obtained from a 10% emulsifiable concentrate). After 24 hours, aphids (Aphis fabae) were placed on the parts of the plant above the soil. The aphids were protected from contact and gas action by means of a special device. The test was carried out at 24° C and 70% relative humidity. In the above tests the compounds according to Example I played insecticidal ingest poison action and systemic insecticidal action.

EXAMPLE 3

Action against Chilo suppressalis

Six rice plants at a time of the variety Caloro were transplanted into plastic pots (diameter at the top = 17 cm) and reared to a height of about 60 cm. Infestation with Chilo suppressalis larvae ($L_1$: 3–4 mm long) took place 2 days after the active substance had been applied in granule form to the paddy water (rate of application: 8 kg of active substance per hectare). Evaluation of the insecticidal action took place 10 days after application of the granules.

The compounds according to Example I were active in the above test against Chilo suppressalis.

EXAMPLE 4

Action against Aulacophora femoralis, Pachmoda and Chortophila larvae

Sterilised compost earth was homogeneously mixed with a wettable powder containing 25% of active substance so that there resulted a rate of application of 8 kg of active substance per hectare.

Young zucchetti plants (Cucumis pepo) were put into plastic pots with the treated soil (3 plants per pot; diameter of pot = 7 cm). Each pot was infected immediately afterwards with 5 Aulacophora femoralis and Pachmoda or Chortophila larvae. The control was carried out 4, 8, 16 and 32 days after depositing the larvae. At 80–100% kill after the first control, a fresh infestation with 5 larvae each was carried out in the same soil sample with 3 new zucchetti plants. If the activity was less than 80%, the remaining larvae remained in the soil sample until the control immediately following. If an active substance at a rate of application of 8 kg/ha still effected a 100% kill, a further control with 4 and 2 kg of active substance per hectare was carried out.

In the above test, the compounds according to Example I displayed action against Aulacophora fermoralis, Pachmoda and Chortophila larvae.

EXAMPLE 5

Action against ticks

A. Rhicephalus bursa

Five adult ticks and 50 tick larvae were counted into a glas tube and immersed for 1 to 2 minutes in 2 ml of an aqueous emulsion from an emulsion series each containing 100, 10, 1 and 0.1 ppm of test substance. The tube was then sealed with a standardised cotton wool plug and placed on its head, so that the active substance emulsion could be adsorbed by the cotton wool.

In the case of the adults evaluation took place after 2 weeks, and in that of the larvae after 2 days. Each test was repeated twice.

B. Boophilus microplus (larvae)

Tests were carried out in each case with 20 OP-sensitive larvae using an analogous dilution series as in the case of test A. (The resistence refers to the tolerability of Diazinon).

The compounds according to Example I acted in these tests against adults and larvae of Rhicephalus bursa and sensitive and OP-resistent larvae of Boophilus microplus.

EXAMPLE 6

Acaracidal action

Phaseolus vulgaris (dwarf beans) have an infested piece of leaf from a mass culture of Tetranychus urticae placed on them 12 hours before the test for acaricidal action. The mobile stages which have migrated are sprayed with the emulsified test preparations from a chromatography atomiser so that the spray broth does not run off. The number of living and dead larvae, adults and eggs are evaluated after 2 to 7 days under a stereoscopic microscope and the result expressed in percentages. During the "interim", the treated plants are kept in greenhouse compartments at 25° C.

The compounds according to Example I were active in the above test against eggs, larvae and adults of Tetranychus urticae.

EXAMPLE 7

Action against soil nematodes

To test the action against soil nematodes, the active substance in each case is applied to and intimately mixed with soil infected with root gall nematodes (Meloidgyne arenaria). Immediately afterwards, tomato cuttings are planted in the thus prepared soil in a series of tests and after a waiting time of 8 days tomato seeds are sown in another test series.

In order to assess the nematocidal action, the galls present on the root are counted 28 days after planting and sowing respectively. In this test the compounds according to Example I display good action against Meloidgyne arenaria.

We claim:

1. The compound O-ethyl-S-n-propyl-O-(2-methylthiomethylphenyl)-thiophosphate.

2. The compound O-ethyl-S-n-propyl-O-(2-methylthiomethyl-4-methylphenyl)-thiophosphate.

3. The compound O-ethyl-S-n-propyl-O-(2-methylthiomethyl-5-methylphenyl)-thiophosphate.

4. The compound O-ethyl-S-n-propyl-O-(2-methylsulfinylmethylphenyl)-thiophosphate.

5. A pesticidal composition for combatting insects, acarids and nematodes which comprises (1) the compound of claim 1 and (2) a carrier.

6. A pesticidal composition for combatting insects, acarids and nematodes which comprises (1) the compound of claim 3 and (2) a carrier.

7. A method for combatting pests selected from the group consisting of insects, acarids and nematodes which comprises applying thereto a pesticidally effective amount of the compound of claim 1.

8. A method for combatting pests selected from the group consisting of insects, acarids and nematodes which comprises applying thereto a pesticidally effective amount of the compound of claim 2.

9. A method for combatting pests selected from the group consisting of insects, acarids and nematodes which comprises applying thereto a pesticidally effective amount of the compound of claim 3.

10. A method for combatting pests selected from the group consisting of insects, acarids and nematodes which comprises applying thereto a pesticidally effective amount of the compound of claim 4.

* * * * *